(12) United States Patent
Dijkstra et al.

(10) Patent No.: US 7,913,563 B2
(45) Date of Patent: Mar. 29, 2011

(54) TECHNIQUE AND PHASED ARRAY TRANSDUCER FOR ULTRASONIC INSPECTION OF COARSE GRAINED, ANISOTROPIC WELDS

(75) Inventors: Frederik Hendrik Dijkstra, Oudenbosch (NL); Khalid Chougrani, Delft (NL); Niels Pörtzgen, Vlaardingen (NL); Cezar Justino Buque, Geesthaacht (DE)

(73) Assignee: Röntgen Technische Dienst B.V., NC Rotterdam (NL)

( * ) Notice: Subject to any disclaimer, the term of this patent is extended or adjusted under 35 U.S.C. 154(b) by 421 days.

(21) Appl. No.: 12/010,520

(22) Filed: Jan. 25, 2008

(65) Prior Publication Data

US 2008/0289425 A1 Nov. 27, 2008

Related U.S. Application Data

(60) Provisional application No. 60/897,463, filed on Jan. 26, 2007.

(51) Int. Cl.
*G01N 29/00* (2006.01)
(52) U.S. Cl. ............... 73/625; 73/620; 73/624; 73/627
(58) Field of Classification Search .............. 73/625, 73/620, 624, 627; 702/159
See application file for complete search history.

(56) References Cited

U.S. PATENT DOCUMENTS

| 4,481,822 | A | * | 11/1984 | Kubota et al. | 73/625 |
|---|---|---|---|---|---|
| 4,495,817 | A | * | 1/1985 | Hunt et al. | 73/624 |
| 5,488,956 | A | | 2/1996 | Bartelt | |
| 5,575,290 | A | | 11/1996 | Teo | |
| 5,992,235 | A | * | 11/1999 | Fischer et al. | 73/617 |
| 6,360,609 | B1 | * | 3/2002 | Wooh | 73/602 |
| 6,799,466 | B2 | * | 10/2004 | Chinn | 73/622 |
| 7,389,694 | B1 | * | 6/2008 | Hay et al. | 73/635 |
| 2006/0009948 | A1 | * | 1/2006 | Wulf et al. | 702/159 |
| 2007/0051177 | A1 | * | 3/2007 | Gifford et al. | 73/620 |
| 2008/0130415 | A1 | * | 6/2008 | Tai | 367/140 |

FOREIGN PATENT DOCUMENTS

| WO | WO2005045598 | * | 5/2005 |
|---|---|---|---|
| WO | WO 2005/108973 | | 11/2005 |

OTHER PUBLICATIONS

Leeuwen. "Applications of Ultrasonic Mode Conversion Techniques." Int. J. Pres. Ves. & Piping 39 (1989) pp. 265-278.
US 5,492,134, 02/1996, Souquest (withdrawn)

* cited by examiner

*Primary Examiner* — Jacques M Saint Surin
(74) *Attorney, Agent, or Firm* — Jacobson Holman PLLC

(57) ABSTRACT

A transducer for generating acoustic waves more particularly for generating compression waves, comprising an array of transmitter elements and an array of receiver elements, at least one wedge for the array of transmitter elements and the array of receiver elements and preferably an acoustical barrier separating the array of transmitter elements and the array of receiver elements. The pitch of the transmitter array varies along the length of the transmitter array.

23 Claims, 4 Drawing Sheets

TECHNIQUE AND PHASED ARRAY TRANSDUCER FOR ULTRASONIC INSPECTION OF COARSE GRAINED, ANISOTROPIC WELDS This is a complete application claiming benefit of provisional 60/897,463 filed on Jan. 26, 2007.

The invention relates to a transducer for generating acoustic waves more particularly for generating compression waves, comprising an array of transmitter elements and an array of receiver elements, at least one wedge for the array of transmitter elements and the array of receiver elements and preferably an acoustical barrier separating the array of transmitter elements and the array of receiver elements.

The invention also relates to a method for inspection of a weld between two plates or pipes, using a transducer for generating acoustic waves, said transducer comprising an array of transmitter elements and an array of receiver elements, a wedge and preferably an acoustical barrier separating the array of transmitter elements and the array of receiver elements.

Ultrasonic examination of anisotropic, coarse-grained materials such as welds consisting primarily on the austenitic phase leads to increased noise, scatter and attenuation of ultrasonic waves when conventional shear wave transducers are used.

It is for this reason that modified ultrasonic techniques were specially designed and are commonly used to overcome this problem. These specially designed ultrasound technologies use longitudinal rather than conventional shear waves. Longitudinal waves are less influenced by the anisotropy of the material to be investigated. Most commonly these transducers are fitted with two physically separated crystals rather than one. One of the crystals acts as a transmitter and the other acts as receiver. In the literature the terminology TRL probes (Transmitter-Receiver Longitudinal) is commonly used to indicate the design features of the transducers described above.

The use of TRL technology for the non-destructive inspection of coarse grained materials with strong anisotropic behavior has been successfully implemented and used, primarily in welds made of austenitic phase but also in ferritic steels, since 1970, both manually (whereby the materials are manually scanned by moving the TRL transducers) and automated (whereby the materials are scanned by several (multiple) TRL transducers that are mounted in a mechanical device that can be moved along a certain direction, e.g. on top of a weld). The corresponding data acquisition is done by a computer or similar recording device. Successful automated ultrasonic examinations of austenitic welds using multiple transducers have been published already in 1976 by RTD. Since that time, RTD has been manufacturing, selling and using TRL transducers for mechanized testing of austenitic welds.

In the construction industry it is common to use coarse-grained, anisotropic welds such as austenitic welds to join austenitic (non-magnetizable) components such as plates or pipes, but also to join other types of material such as ferritic (magnetizable) components. The latter is mostly the case in tanks for storage of Liquefied Natural Gas, where the plates are manufactured out of a high-nickel content (e.g. 9%), ferritic steel alloy and the welds have an austenitic structure.

The present invention relates to an improved technique and phased array transducer which may be advantageously used to inspect these welds.

As stated above, mechanized ultrasonic inspection of coarse-grained, anisotropic welds such as austenitic welds using multiple TRL transducers is known and has been successfully implemented in the past. Most recently RTD submitted U.S. patent application Ser. No. 60/861,964 to a innovative inspection methodology. That new RTD patent application describes how every part of the weld's bevel is hit by an ultrasonic beam as perpendicular as possible, in order to be able to estimate the size of weld defects on the basis of the amplitude of the ultrasonic echo. This requires at least one separate transducer for each bevel facet.

The prior art systems and the invention will now be further discussed referring to the drawing wherein.

DISADVANTAGES OF CURRENT PHASED ARRAY TECHNOLOGY

Figure 1:
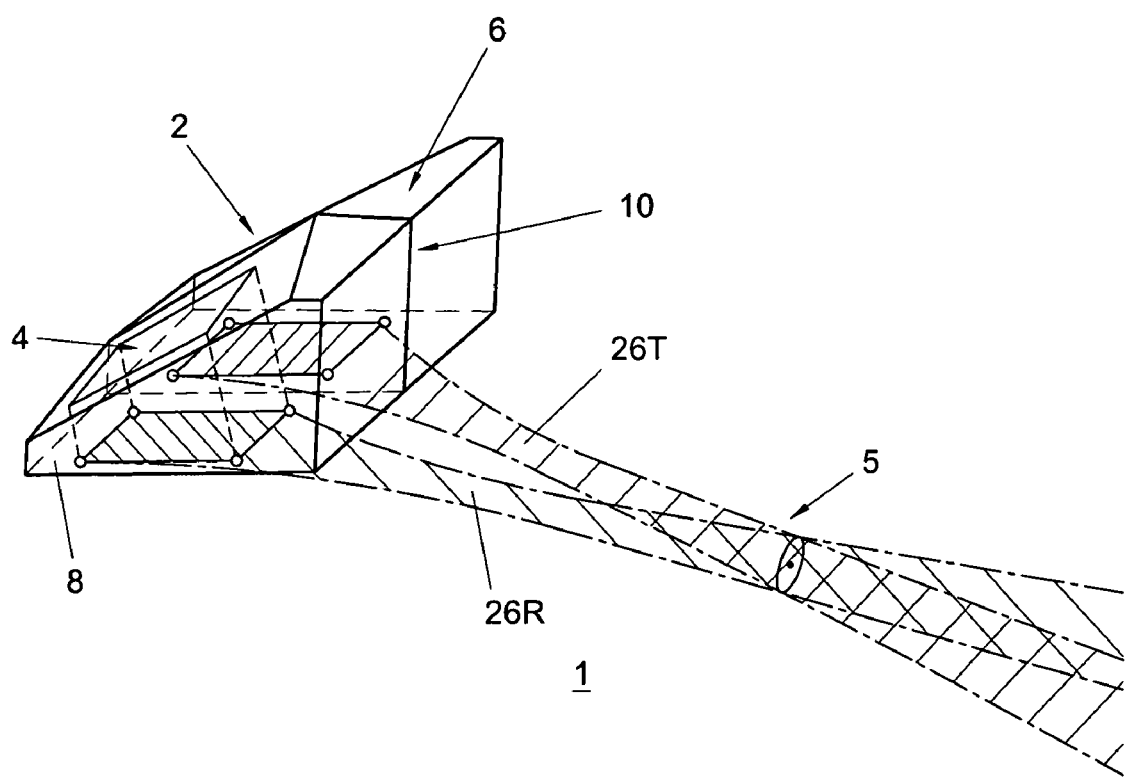
FIG. 1 shows an embodiment of a prior art transducer.

Also the use of phased arrays for the inspection of austenitic welds is known. This method uses a configuration similar to that of a conventional TRL transducer, but in this case the transmitting and the receiving crystal elements are replaced by phased arrays.

The TRL transducer 1 comprises a transmitter element 2, a receiver element 4, a first wedge 6 for the transmitter element 2, a second wedge 8 for the receiver element 4 and a acoustic barrier 10 between the wedges 6,8. The transmitter element 2 generates, in use a transmitter beam 26T and the receiver element receives within a receiving beam 26R. Both beams 26T, 26R intersect at a focal area 5.

Figure 2:
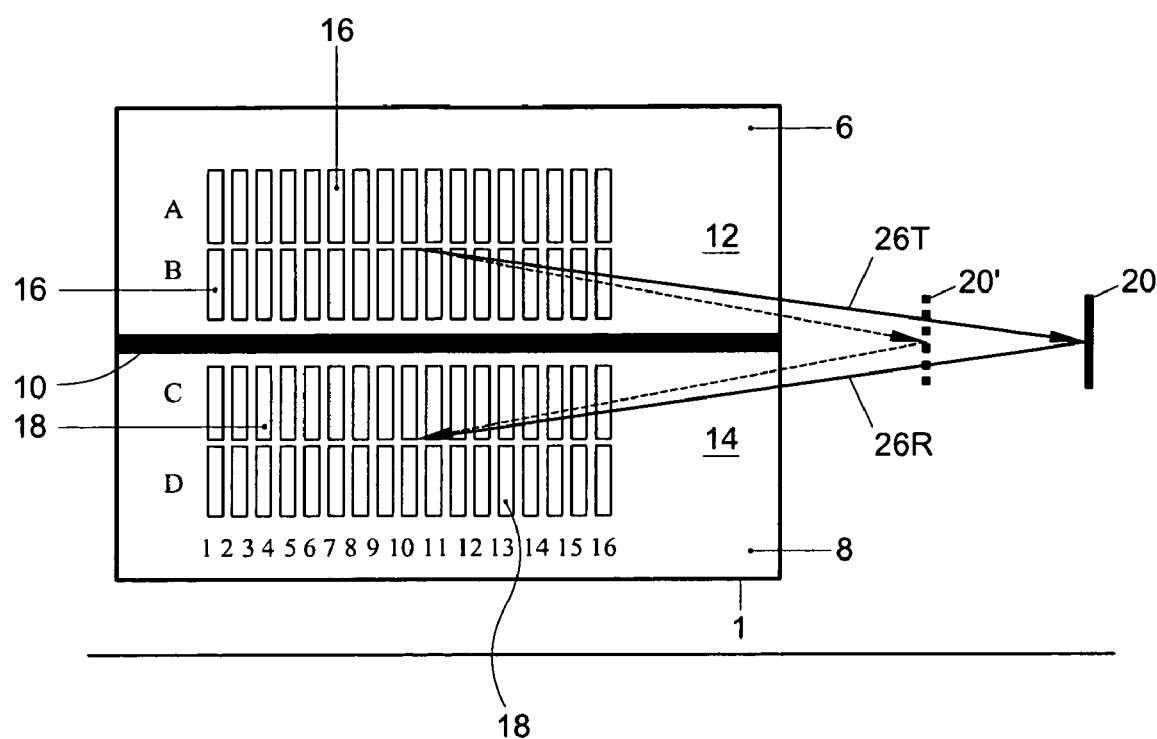
FIG. 2 shows an embodiment of a prior art transducer comprising a transmitter array and a receiver array.

How the crystals 2, 4 of such a transducer as shown in FIG. 1 can be replaced by a transmitter phased array 12 and a receiver phased array 14 is illustrated by FIG. 2, which shows a top view on the wedges 6,8. The dual transmitter array 12 and the dual receiver array 14 are visible and are positioned in a similar position as the crystals shown in FIG. 1. They both consist of a phased array, each typically consisting of two or more rows A, B, C, and D of elements 16, 18. In the example, the transmitter has two rows A, B of transmitter elements 16 and the receiver has two rows C, D of receiver elements 18. Sometimes more than two rows of elements can be used.

Figure 3:
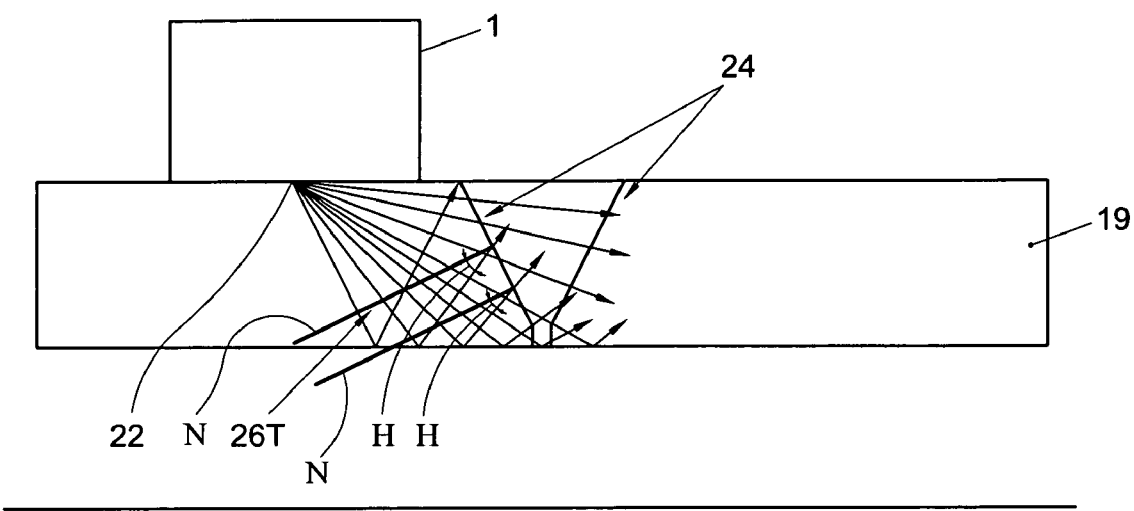
FIG. 3 shows the use of the transducer shown in FIG. 2.

Whereas, in conventional dual TRL transducers, a specified focal distance 20, 20' can be given to a transducer by machining transmitter and receiver under a squint angle, a phased array can do this by varying the transmitting time shifts between elements of rows A relative to elements of rows B and by varying receiving time shifts between elements of row C relative to elements of row D. In this way, "lateral" beam steering is possible. In this way, the focal distance (i.e. the distance at which the beams intersect) can be varied. The angle of incidence of transmitter and receiver can be steered by applying transmitting and receiving time shifts to elements in the rows 1 through 16 as shown in FIG. 3 wherein a plurality of sweeping transmitter beams 26T are shown in an object 19 to be tested wherein each beam comprises an angle of incidence H relative to a normal N of the bevel 24 of the object. Other applications may require other numbers of elements. Corresponding sweeping receiver beams 26R (not shown) are generated by the receiver array 14.

This type of phased array transducer is commonly used to steer the angle and the focal distance, as described above, for inspection of austenitic welds. Usually, the point of incidence 22 of the ultrasonic waves in the object under test (transducer index point 22) essentially remains the same. As a consequence, there is no possibility to ensure that all parts (facets) of the weld bevel 24 are hit perpendicularly by any of the ultrasonic transmitter beams 26T (FIG. 3). Also the corresponding receiver beams 26R should be perpendicular to the corresponding facet of the weld for receiving reflections of the transmitter beam which hits said facet. As a consequence, as explained in U.S. application Ser. No. 60/862,964, this makes it difficult to size defects on the basis of amplitude.

Another disadvantage of the current phased array transducers for this application is the fact that an efficient lateral beam steering using phased arrays requires considerably more (rows of) elements than two (as illustrated in FIG. 2) or three for the transmitter and receiver respectively (preferably eight rows for a transmitter and eight row for a receiver at each side of the transducer in this case). However, to have many more elements would require a transducer with many elements on each side, separated by an acoustic barrier, and thus a much more complicated transducer.

PURPOSE OF THE PRESENT INVENTION

The present invention uses improved phased array transducers (one at each side of the weld). Such transducer may be simple, does not need to have many elements and/or does not have the disadvantages as described above. The objectives which may be obtained alone or in combination are:
1. To enable the transducer index point to move over a certain distance, in order to be able to choose, for perpendicular incidence of each bevel facet, not only an angle, but also a position of the index point;
2. To move away from the inefficient lateral beam steering with only a few elements per row.
3. To move away from the requirement to use more than one row of elements for the transmitter and the receiver respectively.

To achieve the first objective, the transducer will have to have sufficient length and elements to be able to move the index point 22.

The second objective requires an improved phased array configuration.

DESCRIPTION OF THE PRESENT INVENTION

A transducer for generating acoustic waves according to the invention is characterized in that the pitch of the transmitter array varies along the length of the transmitter array. Preferably the pitch of the transmitter array varies along the length of the transmitter array. More preferably the pitch of the transmitter array generally decreases in a direction from a rear of the transducer to a front of the transducer. Preferably the pitch of the receiver array varies along the length of the receiver array. More preferably the pitch of the receiver array generally decreases in a direction from a rear of the transducer to a front of the transducer.

The method according to the invention is characterized in that at least a first and second acoustic beam are generated with different sets of transmitter elements, said beams having a mutually different index point and direction respectively. For this purpose a transducer according to the invention can advantageously be used.

According to an advantageous embodiment the width of the transmitter elements in a direction perpendicular to the length of the transmitter array varies along the length of the transmitter array in a corresponding manner as the pitch of the transmitter array. In such a manner the transmitter which comprises only one row of elements may still be effectively used for generating the desired beams. For example a front part of the transmitter array which comprises a certain number of transmitter elements and which is used for generating a first beam has a relatively small surface area in the direction of the width of the transducer and in the direction of the length of the transducer. A rear part of the transmitter array which comprises the same number of transmitter elements and which is used for generating a second beam has a relatively large surface area in the direction of the width of the transducer and in the direction of the length of the transducer. This means that the first beam is less coherent than the second beam so that the first beam may be used for inspection at a relatively short distance from the transducer and the second beam may be used for inspection at a relatively large distance from the transducer. Because the index point of the first beam differs from the index point of the second beam the angle under which the first beam hits a certain portion of a weld to be inspected at said relatively small distance may be perpendicular to a surface of the weld whereas the angle under which the second beam hits another portion of the weld the be inspected at said relatively large distance may be perpendicular to a surface of the weld too.

Preferably the width of the receiver elements in a direction perpendicular to the length of the receiver array varies along the length of the receiver array in a corresponding manner as the pitch of the receiver array. In such a manner the receiver-array may have characteristics similar a the transmitterarray.

The improved transducer both may have only one array of transmitter elements and only one array of receiver elements, each with sufficient length and a high enough number of elements to accommodate the range of transducer index shift that is necessary for most common wall thicknesses of e.g. tanks, pipes etc. Below, the invention is described for a wall thickness range of 10 to 35 mm. For other thicknesses, similar arrangements can be used, with different parameters such as ultrasonic frequency, number of elements, pitch, element width, and other geometrical characteristics.

In the design and use of conventional TRL transducers on this thickness range, it has been observed that most angles of incidence needed are in the range between 40° and 90° (the latter angle being used for creeping wave transducers). Most focal distances needed are in the range between 15 and 70 mm. Crystal elements have sizes ranging from 8×10 mm (width×length) for small focal distances to 15×25 mm or larger for the larger focal distances.

In addition, it has been observed that, for each transducer, the optimum distance between the beam index point of a transducer and the weld centerline is always in the same order of magnitude as the focal distance of that transducer. This makes sense, because the focal point always has to be located in or near the weld. So larger distances from the weld require a larger focal distance.

For the inspection of the said range of wall thicknesses, the best ultrasonic frequency to be used is typically 2 MHz. It is known that, in order to suppress grating lobes in the ultrasonic beam of phased arrays, the distance between the elements in the array ("pitch") should not exceed a certain value. It is also known that this value is related to the ultrasonic frequency and the beam steering range in the wedge.

For compression wave transducers, the beam steering range in the wedge (for instance made out of Perspex or another similar material) is 10° in order to achieve angles in steel between 40° and 90°. So, if the wedge angle is given a value optimized for an angle in steel in the center of that range, the required sweeping range in the wedge is ±5°. This sweeping range, together with a frequency of 2 MHz, leads to a maximum pitch of approx. 3 mm. At this value, no disturbing grating lobes will be present.

A possible embodiment according to the invention will now be discussed for referring to FIG. 4.

One aspect of the invention is based on the following insights:

For relatively small focal distances a relatively small transmitter is required. A required length is for example 9 mm. Such a transmitter is formed by a set of elements 16 of the phased array of transmitter elements 12 wherein the set comprises a plurality of adjacent elements 16. If the pitch P would be 3 mm the set would only comprise 3 elements which is not sufficient for effective beam steering. In that case a pitch P of 1 mm would be better. This leads to a set comprising 9 adjacent elements 16, which value enables effective beam steering.

For relatively large focal distances a relatively large transmitter is required. A required length is for example 25 mm. Such a transmitter is formed by a set of elements 16 of the phased array of transmitter elements 12 wherein the set comprises a plurality of adjacent elements 16. If the pitch would be 3 mm the selection would comprise 8 elements which is sufficient for effective beam steering. In that case a pitch of 1 mm would not be necessary.

The same applies to the receiver. For relatively small focal distances a relatively small receiver is required. A required length is for example 9 mm. Such a receiver is formed by a set of elements 18 of the phased array 14 of receiver elements 18 wherein the set comprises a plurality of adjacent elements 18. If the pitch P would be 3 mm the selection would only comprise 3 elements 18 which is not sufficient for effective beam steering. In that case a pitch of 1 mm would be better. This leads to a set comprising 9 adjacent elements, which value enables effective beam steering.

For relatively large focal distances a relatively large receiver is required. A required length is for example 25 mm. Such a receiver is formed by a set of elements 18 of the phased array of receiver elements 14 wherein the set comprises a plurality of adjacent elements 18. If the pitch would be 3 mm the set would comprise 8 elements which is sufficient for effective beam steering. In that case a pitch of 1 mm would not be necessary.

Therefore, a receiver transducer and a transmitter transducers according to one aspect of the invention each comprises the use of phased arrays with a non-constant pitch P over the array length, for instance varying from 1 mm at the transducer's front 32 to 3 mm at the rear 30 of the transducer. The software (i.e. the software module that calculates the delays for the array's elements) should of course support this.

For example a set of elements 12 at the transducer's front 32 can be used for relatively small focal distances by generating a beam 26Ts having a relatively large beam spread (measured in an angle fs perpendicular to a plane Q of the transducers) at those relatively small focal distances for obtaining a relatively small beam width (measured in a length Ds) at those relatively small focal distances wherein the a set of elements at the transducer's rear 30 can be used for relatively large focal distances by generating a beam 26 Tl having a relatively small beam spread (measured in angle fl perpendicular to the plane Q) at those relatively large focal distances for obtaining a relatively small beam width (measured in a length Dl) at those relatively large focal distances (see FIG. 4).

The index point 22 of the beam 26Ts lays relatively close to the front 32 of the transducer so that the beam 26Ts hits the weld substantially perpendicular.

The index point 22' of the beam 26Tl lays relatively close to the rear 30 of the transducer so that the beam 26Ts also hits the weld substantially perpendicular.

An array consisting of 32 elements, using this principle will have a length of 64 mm.

An additional advantage of the use of a non-constant pitch is that grating lobes are even further suppressed. This is caused by the fact that the contributions of the grates are not in phase, so destructive interference reduces the sound pressure in the grating lobe.

Figure 4A:
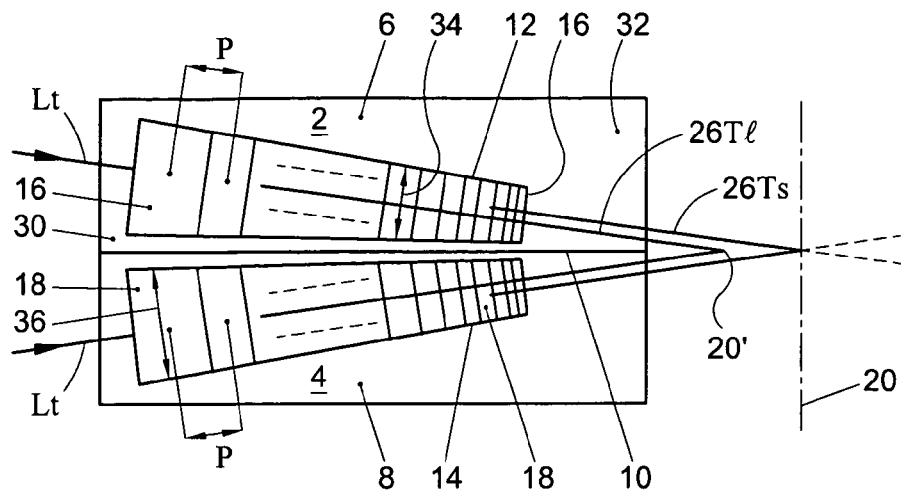
FIG. 4 shows the use of a possible embodiment of a transducer according to the present invention.
Figure 4B:
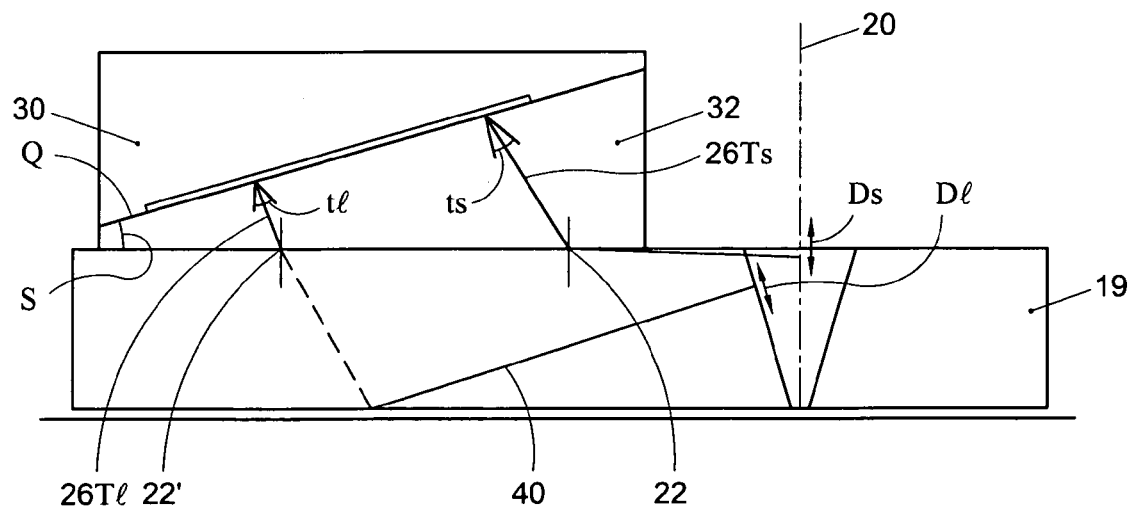

The same applies mutates mutandis for the corresponding receiver beam 26Rs which coincides in FIG. 4B with the transmitter beam 26Ts and for the corresponding receiver beam 26Rl which coincides in FIG. 4B with the transmitter beam 26Tl.

Hence it holds for the embodiment according to FIG. 4 that the transducer for generating acoustic waves more particularly for generating compression waves, comprising an array 12 of transmitter elements 16 and an array 14 of receiver elements 18, at least one wedge 6,8 for the array of transmitter elements and the array of receiver elements. The array 12 may be fixed on the wedge 6. It is also possible that the transducer comprises a first wedge 6 for the transmitter array 12 and a second wedge 8 for the receiver array 14. Preferably it comprises an acoustical barrier 10 separating the array of transmitter elements and the array of receiver elements. In this example the acoustical barrier 10 extends between the first wedge 6 and the second wedge 8. The pitch of the transmitter array 12 varies along the length Lt of the transmitter array. The pitch of the transmitter array 12 varies along substantially the full length of the transmitter array. The pitch of the transmitter array 12 generally decreases in a direction from a rear 30 of the transducer to a front 32 of the transducer. The pitch of the receiver array 14 varies along the length Lr of the receiver array. The pitch of the receiver array generally decreases in a direction from a rear 30 of the transducer to a front 32 of the transducer.

To accommodate the requirement of a larger width for larger focal distances, the invention also comprises a transmitter array 12 and a receiver array 14, each with varying width 34, 36 (e.g varying from 8 to 15 mm). The values mentioned are only examples, and different applications could require values that differ from this example.

A set of elements 16 at the transducers front 32 have a relatively small width 34 and can be used for relatively small focal distances 20 by generating a transmitter beam 26Ts having a relatively large beam spread (measured in an angle gs parallel to the plane Q of the transducers and perpendicular to the angle fs) at those relatively small focal distances 20 for obtaining a relatively small beam width (measured as a length ds in the bevel 24 and perpendicular to the distance Ds) at those relatively small focal distances 20.

A set of elements 16 at the transducers rear 30 have a relatively large beam width 34 and can be used for relatively large focal distances 20' by generating a transmitter beam 26Tl having a relatively small beam spread (measured in an angle gl parallel to the plane Q of the transducers and perpendicular to the angle fl) at those relatively large focal distances 20' for obtaining a relatively small beam width (measured as a length dl in the bevel 24 and perpendicular to the distance Dl) at those relatively large focal distances 20'.

Other sets of transmitter elements 16 laying between the above discussed sets may be used for generating other transmitter beams at focal distances laying between the focal distances 20, 20'.

The same applies to the receiver elements 18. A set of elements 18 at the transducers front 32 have a relatively small width 36 and can be used for relatively small focal distances 20 by generating a receiver beam 26Rs having a relatively large beam spread (measured in an angle gs parallel to the plane Q of the transducers and perpendicular to the angle fs) at those relatively small focal distances 20 for obtaining a relatively small receiver beam width (measured as a length ds in the bevel 24 and perpendicular to the distance Ds) at those relatively small focal distances 20.

A set of receiver elements 18 at the transducers rear 30 have a relatively large beam width 36 and can be used for relatively large focal distances 20' by generating a receiver beam 26Rl having a relatively small beam spread (measured in an angle gl parallel to the plane Q of the transducers and perpendicular to the angle fl) at those relatively large focal distances 20' for obtaining a relatively small beam width (measured as a length dl in the bevel 24 and perpendicular to the distance Dl) at those relatively large focal distances 20'.

Other sets of receiver elements 18 laying between the above discussed sets may be used for generating other receiver beams at focal distances laying between the focal distances 20, 20'.

Hence for the embodiment shown in FIG. 4 it holds that the width 34 of the transmitter elements 16 in the direction perpendicular to the length Lt of the transmitter array generally decreases in a direction from a rear 30 of the transducer to a front 32 of the transducer. The width 34 of the transmitter elements 16 in a direction perpendicular to the length Lt of the transmitter array 12 varies along the length Lt of the transmitter array in a corresponding manner as the pitch of the transmitter receiver array. The width 36 of the receiver elements in the direction perpendicular to the length of the receiver array generally decreases in a direction from a rear 32 of the transducer to a front 34 of the transducer. The width 36 of the receiver elements 16 in a direction perpendicular to the length Lr of the receiver array 14 varies along the length Lr of the receiver array in a corresponding manner as the pitch of the receiver array. The pitch of the transmitter array and the pitch of the receiver array generally vary in the same manner. The width of the transmitter elements and the width of the receiver elements generally vary in the same manner. The invention is however not limited to this example.

The embodiment further comprises the transmitter and receiver halves of the transducer are rotated relative to each other (during manufacturing), in such a way that the center lines Lr, Lt of both arrays intersect at a distance of approx. 15 mm before the front of the transducer. By doing this, beams generated by two corresponding areas of the transmitter and receiver array will always intersect at a point in the material which is at approximately the same projected distance in front of the transducer. The distance may vary for different probe angles, but is accurate enough for practical purposes. In this way it is not required to use multiple receiver arrays and multiple transmitter arrays as discussed in relation with FIG. 2.

The above transducer can be used for at least all techniques commonly used for the ultrasonic inspection of coarse-grained anisotropic welds. These techniques include primary and secondary creeping waves, direct and indirect insonification and tandem technique (a special embodiment of tandem technique is round trip tandem, whereby transmitter and receiver index points coincide). See for example U.S. patent application Ser. No. 60/861,964 and the article Applications of Ultrasonic Mode Conversion Techniques (W. H. van Leeuwen; Int. J. Pres. Ves. & Piping 39 (1989) 265-278).

In FIG. 4A a top view (as in FIG. 2) and in FIG. 4 B a side view (as in FIG. 3) of the transducer according to an embodiment of the invention is shown. The top view shows the transmitter and receiver array 12,14. The complete halves of the transducer, both having a wedge angle S optimized for the center 40 of the beam sweep range in steel, have been rotated so that the centerlines Lr, Lt of transmitter and receiver intersect at approx. 15 mm in front of the probe. In the top view, some of the elements 16, 18 forming the array (not all) are shown, having the smallest pitch P at the front of the transducer and the larger pitch values (not shown) at the rear.

The side view shows how the beams enter the component 19 under test. A creeping wave 26Ts (under 90° with the normal) is generated by the front part of the transducer and inspects the near surface area of the weld. Another beam 26Tl (which has an angle of 70° after wave mode conversion at the bottom of the steel plate) inspects one of the weld bevels, hitting the bevel perpendicularly.

Only the beam center lines 40 have been drawn. A similar method and transducer can be used on the other side of the weld for inspecting the other side of the weld.

For moving the index point 22 of a beam, different sets of elements are used. For example 8 transmitter elements laying at the rear 30 of the array are used for generating a transmitter beam 26Tl with a relatively small beam width (measured in a length Dl) at larger distances and an index point 22' (see FIG. 4) which is at a position such that the beam at least substantially hits the weld perpendicularly to be inspected. Further 8 transmitter elements laying at the front 32 of the array are used for generating a receiver beam 26Ts with a relatively small beam width (measured in a length Ds) at smaller distances and an index point 22 (see FIG. 4) which is at a position such that the beam falls at least substantially perpendicular at the weld to be inspected. The same applies mutatis mutandis for sets of transmitter elements laying in between these two sets of transmitter elements.

The same applies mutatis mutandis for selected sets of receiver elements. In the present example 8 receiver elements laying at the rear 30 of the array are used in combination with the 8 transmitter elements laying at the rear 30 for obtaining a focus point 20' at a desired relatively large distance and that 8 receiver elements are used laying at the front 32 for obtaining a focus point 20 at a desired relatively small distance. The same applies mutatis mutandis for sets of receiver elements laying in between these two sets of receiver elements. Selecting an index point 22, 22' at a desired position as discussed above can according to an aspect of the invention also be carried out with convention transducers such as shown in FIG. 2. In that case the transducer should be provided with a sufficient number of transmitter and receiver elements in order to obtain a sufficient variation in possible positions of the index point.

The invention claimed is:

1. A transducer for generating acoustic waves more particularly for generating compression waves, comprising an array of transmitter elements and an array of receiver elements, at least one wedge for the array of transmitter elements and the array of receiver elements and preferably an acoustical barrier separating the array of transmitter elements and the array of receiver elements, characterized in that the pitch of the transmitter array varies along the length of the transmitter array, such that the pitch of the transmitter array generally decreases in a direction from a rear of the transducer to a front of the transducer, and in that the width of the transmitter elements in a direction perpendicular to the length of the transmitter array varies along the length of the transmitter array in a corresponding manner as the pitch of the transmitter array, such that the width of the transmitter elements in the direction perpendicular to the length of the transmitter array generally decreases in a direction from a rear of the transducer to a front of the transducer.

2. The transducer according to claim 1, characterized in that the pitch of the transmitter array varies along substantially the full length of the transmitter array.

3. The transducer according to claim 1, characterized in that the pitch of the receiver array varies along the length of the receiver array.

4. The transducer according to claim 3, characterized in that the pitch of the receiver array generally decreases in a direction from a rear of the transducer to a front of the transducer.

5. The transducer according to claim 1, characterized in that the width of the receiver elements in a direction perpendicular to the length of the receiver array varies along the length of the receiver array in a corresponding manner as the pitch of the receiver array.

6. The transducer according to claim 5, characterized in that the width of the receiver elements in the direction perpendicular to the length of the receiver array generally decreases in a direction from a rear of the transducer to a front of the transducer.

7. The transducer according to claim 2, characterized in that the pitch of the transmitter array and the pitch of the receiver array generally vary in the same manner.

8. The transducer according to claim 1, characterized in that the width of the transmitter elements and the width of the receiver elements generally vary in the same manner.

9. The transducer according to claim 1, characterized in that a distance between the longitudinal center line of the transmitter array and the longitudinal center line of the receiver array generally decreases in a direction from the rear of transducer to the front of the transducer.

10. The transducer according to claim 1, characterized in that the transducer is provided with at least one wedge for at least the transmitter array wherein a height from the at least one wedge perpendicular to the transmitter array increases in the direction from the rear of the transducer to the front of the transducer.

11. The transducer according to claim 10, characterized in that the transmitter array is fixed on the wedge.

12. The transducer according to claim 11, characterized in that the receiver array is fixed on the wedge.

13. The transducer according to claim 1, wherein the transducer is provided with a first wedge for the transmitter array and a second wedge for the receiver array wherein the height of each wedge perpendicular to the transmitter array increases in the direction from the rear of the transducer to the front of the transducer.

14. A method for inspection of a weld between two plates or pipes, using a transducer for generating acoustic waves, said transducer comprising an array of transmitter elements and an array of receiver elements, a wedge and preferably an acoustical barrier separating the array of transmitter elements and the array of receiver elements, characterized in that at least a first and second acoustic beam are generated with different sets of transmitter elements, said beams having a mutually different index point and direction respectively, and characterized in that at least a first and second acoustic beam are generated with different sets of transmitter elements, said beams having a mutually different index point and direction respectively so that the first beam falls on a first part of the weld in a direction at least substantially perpendicular to this first part of the weld and the second beam falls on a second part of the weld in a direction at least substantially perpendicular to this second part of the weld wherein the first part of the weld and the second part of the weld differ.

15. The method according to claim 14, characterized in that for transmitting more than two acoustic beams in different directions more than two different sets of transmitter elements are selected such that by means of each of such a set a beam with an index point and direction is obtained such that the beam falls on a part if the weld in a direction at least substantially perpendicular to this part of the weld.

16. The method according to claim 14, characterized in that different sets of transmitter elements are selected for generating different beams with different index points.

17. The method according to claim 14, characterized in that different sets of transmitter elements have different distances from a center of the set to a front of the transducer.

18. The method according to claim 14, characterized in that a set of transmitter elements comprises a plurality of transmitter elements laying adjacent to each other.

19. The method according to claim 14, characterized in that a transmitter beam is focused by selecting a delay between elements of a set of transmitter elements.

20. The method according to claim 14, characterized in that the transmitter array has a configuration of transmitter elements which is the same as the configuration of receiver elements of the receiver array.

21. The method according to claim 20, characterized in that sets of receiver elements are used for receiving reflected beams which sets of receiver elements correspond with the selected sets of transmitter elements respectively.

22. The method according to claim 21, characterized in that a receiver beam is focused by selecting a delay between elements of a set of receiver elements.

23. The method according to claim 14, characterized in that the pitch of the transmitter array varies along the length of the transmitter array.

* * * * *